(12) United States Patent
Kotanko et al.

(10) Patent No.: US 12,226,563 B2
(45) Date of Patent: Feb. 18, 2025

(54) VASCULAR ACCESS IDENTIFICATION AND VALIDATION SYSTEM

(71) Applicant: FRESENIUS MEDICAL CARE HOLDINGS, INC., Waltham, MA (US)

(72) Inventors: Peter Kotanko, New York, NY (US); Stephan Thijssen, New York, NY (US); Anna Meyring-Wösten, Münster (DE); Hanjie Zhang, Rutherford, NJ (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 1054 days.

(21) Appl. No.: 17/090,989

(22) Filed: Nov. 6, 2020

(65) Prior Publication Data

US 2021/0138130 A1 May 13, 2021

Related U.S. Application Data

(60) Provisional application No. 62/932,601, filed on Nov. 8, 2019.

(51) Int. Cl.
*A61M 1/36* (2006.01)
*A61M 39/02* (2006.01)
(Continued)

(52) U.S. Cl.
CPC ........ *A61M 1/3653* (2013.01); *A61M 1/3655* (2013.01); *A61M 39/0247* (2013.01); *G16H 10/60* (2018.01); *A61M 1/1601* (2014.02); *A61M 2039/0258* (2013.01); *A61M 2039/0276* (2013.01); *A61M 2205/3576* (2013.01); *A61M 2205/502* (2013.01); *A61M 2205/52* (2013.01);
(Continued)

(58) Field of Classification Search
None
See application file for complete search history.

(56) References Cited

U.S. PATENT DOCUMENTS

| 6,264,613 | B1 * | 7/2001 | Pfeiffer | ................. A61B 5/028 600/394 |
| 2004/0176813 | A1 | 9/2004 | Gelfand et al. | |

(Continued)

OTHER PUBLICATIONS

Gibbons, "Primary Vascular Access", European Journal of Vascular and Endovascular Surgery, vol. 31, Issue 5, 523-529.

(Continued)

*Primary Examiner* — Jenna Zhang
(74) *Attorney, Agent, or Firm* — Lando & Anastasi, LLP

(57) ABSTRACT

Techniques for vascular access identification and validation are disclosed. The techniques include: directly or indirectly acquiring an acquired value for a parameter that is a function of oxygen saturation (SO2) of a sample of blood in or obtained from a vascular access device (VAD) disposed in a subject; performing an evaluation of the acquired value at least by comparing the acquired value with one or more reference values; and responsive to the evaluation of the acquired value, assigning an identity classification to the VAD, wherein the identity classification is one of a central venous catheter (CVC), an arteriovenous access device (AVA), or another class of VAD.

17 Claims, 5 Drawing Sheets

(51) Int. Cl.
*G16H 10/60* (2018.01)
*A61M 1/16* (2006.01)

(52) U.S. Cl.
CPC . *A61M 2205/60* (2013.01); *A61M 2205/6009* (2013.01); *A61M 2230/20* (2013.01); *A61M 2230/205* (2013.01)

(56) References Cited

U.S. PATENT DOCUMENTS

| | | | |
|---|---|---|---|
| 2007/0299384 | A1 | 12/2007 | Faul et al. |
| 2009/0156916 | A1* | 6/2009 | Wang ............... A61B 5/150503 600/339 |
| 2012/0045791 | A1* | 2/2012 | Ghobadi ............ A61B 5/15003 435/29 |
| 2012/0065485 | A1* | 3/2012 | Benni ................ A61B 5/14551 600/323 |
| 2016/0374612 | A9* | 12/2016 | Hulvershorn ......... A61M 5/427 600/509 |
| 2018/0218792 | A1* | 8/2018 | Muhsin ................... G16Z 99/00 |
| 2018/0322248 | A1* | 11/2018 | Alisuag ................. G16H 40/67 |
| 2020/0187870 | A1* | 6/2020 | Bosque ................ A61B 5/0002 |

OTHER PUBLICATIONS

Harrison et al., "Central venous oxygen saturation: a potential new marker for circulatory stress in haemodialysis patients?", Nephron Clinical practice, 2014; 128: 57-60.
Hasan, Handbook of Blood Gas/Acid-Base Interpretation, Springer, 2009.
Jones et al., "Continuous measurements of oxygen saturation during haemodialysis", Nephrology, dialysis, transplantation: official publication of the European Dialysis and Transplant Association, European Renal Association, 1992; 7: 110-116.
Mickley, "Central vein obstruction in vascular access", European Journal of Vascular and Endovascular Surgery, Oct. 2006, 32(4): 439-44.
Roy-Chaudhury et al., "Hemodialysis Vascular Access Dysfunction: A Cellular and Molecular Viewpoint", Journal of the American Society of Nephrology, Apr. 2006, 17: 1112-1127.
Santoro et al., "Vascular access for hemodialysis: current perspectives", International Journal of Nephrology and Renovascular Disease, Jul. 2014; 7: 281-94.
Extended European Search Report from corresponding European Application No. 20884182.5 dated Oct. 13, 2023.

* cited by examiner

Histogram of mean oxygen saturation in treatments with documented central venous catheter Histogram of mean oxygen saturation in treatments with documented arterio-venous catheter

VASCULAR ACCESS IDENTIFICATION AND VALIDATION SYSTEM

RELATED APPLICATIONS

This application claims the benefit of U.S. Provisional Patent Application Ser. No. 62/932,601, titled "Vascular Access Identification & Validation System," filed Nov. 8, 2019, which is hereby incorporated by reference.

BACKGROUND

Hemodialysis is a treatment in which an artificial kidney (hemodialyzer) is used to remove waste and excess fluid from the blood. In hemodialysis, an access, commonly referred to as a vascular access, is made into the blood vessels of the patient. The two main types of vascular access devices are a central venous catheter (CVC) and an arteriovenous access (AVA).

A CVC is a catheter inserted into a vein, usually in the neck or below the collarbone. AVAs includes both arteriovenous fistulas and grafts. An arteriovenous fistula is made by joining an artery and a vein under the skin, usually of the arm. When the artery and vein are joined, the pressure inside the vein increases, making the walls of the vein stronger. The stronger vein can then receive the needles used for hemodialysis. Similarly, an arteriovenous graft is made by joining an artery and vein under the skin. However, rather than being directly joined, they are joined with a mechanical device, typically a plastic tube. Current standard practice requires the identity of a dialysis patient's vascular access (i.e., a CVC or AVA) to be manually recorded in the patient's electronic health record (EHR).

SUMMARY OF THE INVENTION

The disclosure relates, inter alia, to novel methods of identifying and/or validating an identification of a subject's vascular access device. The disclosure provides novel methods of identifying a vascular access device (e.g., a central venous catheter (CVC) versus an arteriovenous access (AVA)), comprising, inter alia: directly or indirectly acquiring one or more value(s) of oxygen saturation ($SO_2$) of a sample of extracorporeal blood obtained from the subject's vascular access device; making an assessment of whether said one or more value(s) is indicative of venous oxygen saturation ($SvO_2$) or arterial oxygen saturation ($SaO_2$); and based on said assessment, making a determination of the identity of the subject's vascular access device (e.g., a CVC or an AVA).

In an embodiment, the disclosure is based, inter alia, on the discovery that manual recordation of a patient's vascular access device is inaccurate. Therefore, the methods described herein provide for, inter alia, methods to identify a vascular access device, methods to validate the identity of a vascular access device, and methods to detect and correct an inaccurate identification of a vascular access device.

In general, in one aspect, a method includes: directly or indirectly acquiring an acquired value for a parameter that is a function of oxygen saturation ($SO_2$) of a sample of blood in or obtained from a vascular access device (VAD) disposed in a subject; performing an evaluation of the acquired value at least by comparing the acquired value with one or more reference values; and responsive to the evaluation of the acquired value, assigning an identity classification to the VAD, wherein the identity classification is one of a central venous catheter (CVC), an arteriovenous access device (AVA), or another class of VAD.

The method may further include assessing whether the acquired value is indicative of venous oxygen saturation ($SvO_2$) or arterial oxygen saturation ($SaO_2$).

The method may further include comparing the identity classification of the VAD with a record associated with the subject, to determine whether the subject has a class of VAD indicated by the record. The method may further include addressing an inconsistency between the identity classification and the record, at least by flagging the inconsistency for human review. The method may further include addressing an inconsistency between the identity classification and the record, at least by correcting the record to reflect the identity classification of the VAD.

The one or more reference values may include one or more of a predetermined value characteristic of arterial oxygen saturation ($SaO_2$) or a predetermined value characteristic of venous oxygen saturation ($SvO_2$).

The method may further include memorializing the identity classification of the VAD in a record associated with the patient.

In general, in one aspect, one or more non-transitory computer-readable media store instructions that, when executed by one or more processors, cause the one or more processors to perform operations including: directly or indirectly acquiring an acquired value for a parameter that is a function of oxygen saturation ($SO_2$) of a sample of blood in or obtained from a vascular access device (VAD) disposed in a subject; performing an evaluation of the acquired value at least by comparing the acquired value with one or more reference values; and responsive to the evaluation of the acquired value, assigning an identity classification to the VAD, wherein the identity classification is one of a central venous catheter (CVC), an arteriovenous access device (AVA), or another class of VAD.

The operations may further include assessing whether the acquired value is indicative of venous oxygen saturation ($SvO_2$) or arterial oxygen saturation ($SaO_2$).

The operations may further include comparing the identity classification of the VAD with a record associated with the subject, to determine whether the subject has a class of VAD indicated by the record. The operations may further include addressing an inconsistency between the identity classification and the record, at least by performing one or more of (a) flagging the inconsistency for human review or (b) correcting the record to reflect the identity classification of the VAD.

The one or more reference values may include one or more of a predetermined value characteristic of arterial oxygen saturation ($SaO_2$) or a predetermined value characteristic of venous oxygen saturation ($SvO_2$).

The operations may further include memorializing the identity classification of the VAD in a record associated with the patient.

In general, in one aspect, a blood monitoring system includes: a sensor configured to measure a value indicative of an oxygen saturation ($SO_2$) in blood obtained from a vascular access device (VAD) disposed in a dialysis patient; one or more processors; and one or more non-transitory computer-readable media storing instructions that, when executed by the one or more processors, cause the one or more processors to perform operations including: receiving the value from the probe; and identifying a type of the VAD based at least on the value.

The blood monitoring system may further include a display, and the operations may further include displaying the type of the VAD via the display.

The type of the VAD may include one or more of a central venous catheter (CVC) or an arteriovenous access device (AVA).

The one or more processors may be communicatively coupled to a dialysis machine. The operations may further include providing information indicative of the type of the VAD to the dialysis machine.

The one or more processors may be communicatively coupled to a central server storing an electronic health record (EHR) of the dialysis patient. The operations may further include providing information indicative of the type of the VAD to the central server to update the EHR of the dialysis patient.

According to at least one aspect, a method of identifying a class of a vascular access device (VAD) disposed in a subject is provided. The method includes directly or indirectly acquiring an acquired value for a parameter that is a function of oxygen saturation ($SO_2$) of a sample of blood in or obtained from the VAD, performing an evaluation of the acquired value at least by comparing the acquired value with one or more reference values, and responsive to the evaluation the acquired value, assigning an identity classification to the VAD, wherein the identity classification is one of a central venous catheter (CVC), an arteriovenous access device (AVA), or another class of VAD.

In some examples, the acquiring includes directly acquiring.

In some examples, the acquiring includes providing a detection probe into contact with, or into sufficiently close proximity with, the sample of blood to allow a determination of $SO_2$ in the sample of blood to be made. The method may further include determining a value for a parameter that is a function of $SO_2$ with the probe.

In some examples, the method further includes comparing the acquired value with a reference value. Comparing the acquired value may include determining if the acquired value has a predetermined relationship with the reference value. The predetermined relationship may be that the acquired value is equal to or less than, e.g., less than, the reference value. The method may further include classifying the device as a CVC. The predetermined relationship may be that the acquired value is equal to or greater than, e.g., greater than, the reference value. The method may further include classifying the device as an AVA.

In some examples, the method further includes making an assessment of whether the acquired value is indicative of venous oxygen saturation ($SvO_2$) or arterial oxygen saturation ($SaO_2$).

In some examples, the method further includes memorializing the acquired value.

In some examples, the method further includes memorializing the evaluation of the acquired value.

In some examples, the method further includes classifying the VAD as a CVC or an AVA.

In some examples, the method further includes memorializing the classification of the VAD as a CVC or an AVA, for example in a record that includes an identifier for the subject, e.g., in a medical record for the subject.

In some examples, the method further includes classifying the VAD. The method may further include comparing the classification of the VAD with a reference, e.g., the type of VAD installed in the subject, e.g., as indicated in a record comprising an identifier for the subject and an identifier for the type of VAD installed, e.g., a medical record. The method may further include, responsive to the classification, selecting or performing an action. The action may include confirming the subject has the correct type of VAD. The action may include confirming the subject has the incorrect type of VAD. The action may include removing the VAD from the subject. The action may include installing a different type of VAD in the subject.

In some examples, the method further includes comparing a determination to a record (e.g., an electronic health record) of the identity of the subject's vascular access device, optionally, if said determination is inconsistent with said record, correcting the inconsistency in the record to reflect said determination, and optionally using said determination in a method of assessing (e.g., predicting) the prognosis of a disorder (e.g., a renal disorder), wherein the subject has been diagnosed with said disorder (e.g., a renal disorder).

In some examples, acquiring a value for a parameter that is a function of $SO_2$ includes acquiring multiple, e.g., two, three, four, five, six, seven, eight, nine, ten or more values for $SO_2$. The acquired value may be a function, e.g., the average, of multiple, e.g., two, three, four, five, six, seven, eight, nine, ten or more values for $SO_2$. The method may further include determining an average value of multiple, e.g., two, three, four, five, six, seven eight, nine, ten or more observed values for $SO_2$. A value for $SO_2$ may be obtained during a process which includes removing blood from and returning the blood to a subject, e.g., hemodialysis treatment. A value for $SO_2$ may be obtained within a preselected time frame, e.g., within a preselected time after initiation of a procedure, e.g., after installation of the VAD, or initiation of an extracorporeal treatment, e.g., hemodialysis treatment. The procedure may be hemodialysis. A value of $SO_2$ may be obtained during the first hour of a hemodialysis treatment.

In some examples, the evaluation includes making a comparison of the acquired value to a predetermined value characteristic of $SaO_2$ and/or making a comparison of the acquired value to a predetermined value characteristic of $SvO_2$. The predetermined value of $SaO_2$ may be a range classified as normal $SaO_2$ by standard medical practice. The value of $SaO_2$ may be expressed as a percentage of total hemoglobin saturated with oxygen. The reference value may be a value for $SaO_2$. For example, the reference value of $SaO_2$ may be a range of 90-100%, 91-100%, 92-100%, 93-100%, 94-100%, 95-100%, 96-100%, 97-100%, 98-100%, or 99-100%. The reference value of $SaO_2$ may be 94-100%. The reference value of $SaO_2$ may be above 90%. The value of $SvO_2$ may be expressed as a percentage of total hemoglobin saturated with oxygen. The reference value of $SvO_2$ may be a range classified as $SvO_2$ normal by standard medical practice. For example, the reference value of $SvO_2$ may be 60-80%, 61-80%, 62-80%, 63-80%, 64-80%, 65-80%, 66-80%, 67-80%, 68-80%, 69-80%, 70-80%, 65-75%, 65-76%, 65-77%, 65-78%, or 65-79%. The reference value of $SvO_2$ may be 60-80%. The reference value of $SvO_2$ may be 65-80%.

In some examples, the subject's vascular access device is identified as a CVC if the $SO_2$ of the sample of extracorporeal blood meets (e.g., corresponds with, satisfies, or falls within) a predetermined range (e.g., a range including the minimum and maximum values of the range, and in some cases plus or minus a window of variability (e.g., +/−0.5%, +/−1%, +/−5%, or +/−10%)). For example, the predetermined range may be 60-80%, 61-80%, 62-80%, 63-80%, 64-80%, 65-80%, 66-80%, 67-80%, 68-80%, 69-80%, 70-80%, 65-75%, 65-76%, 65-77%, 65-78%, or 65-79%. The predetermined value of $SvO_2$ may be 60-80%. The predetermined range of $SvO_2$ may be 65-80%.

In some examples, the subject's vascular access device is identified as an AVA if the $SO_2$ of the sample of extracorporeal blood meets (e.g., corresponds with, satisfies, or falls within) a predetermined range (e.g., a range including the minimum and maximum values of the range, and in some cases plus or minus a window of variability (e.g., +/−0.5%, +/−1%, +/−5%, or +/−10%)). For example, the predetermined range may be 90-100%, 91-100%, 92-100%, 93-100%, 94-100%, 95-100%, 96-100%, 97-100%, 98-100%, or 99-100%. The predetermined value of $SaO_2$ may be 94-100%. The predetermined value of $SaO_2$ may be above 90%.

In some examples, if the assessment is indicative of $SvO_2$, the method includes determining that the subject's vascular access device is a CVC.

In some examples, if the assessment is indicative of $SaO_2$, the method includes determining that the subject's vascular access device is an AVA.

In some examples, the acquired value is indicative of $SvO_2$ if the acquired value falls within a predetermined range. The predetermined range may be a range classified as $SvO_2$ normal by standard medical practice. For example, the predetermined range may be 60-80%, 61-80%, 62-80%, 63-80%, 64-80%, 65-80%, 66-80%, 67-80%, 68-80%, 69-80%, 70-80%, 65-75%, 65-76%, 65-77%, 65-78%, or 65-79%. The predetermined range may be 60-80%. The predetermined range may be 65-80%.

In some examples, the value is indicative of $SaO_2$ if said value falls within a predetermined range. The predetermined range may be a range classified as normal $SaO_2$ by standard medical practice. The predetermined range may be expressed as a percentage of total hemoglobin saturated with oxygen. For example, the predetermined range may be 90-100%, 91-100%, 92-100%, 93-100%, 94-100%, 95-100%, 96-100%, 97-100%, 98-100%, or 99-100%. The predetermined range may be 94-100%. The predetermined range may be above 90%.

In some examples, the value of $SO_2$ is measured using a blood gas analyzer (e.g., as described herein).

In some examples, the value of $SO_2$ is measured using a Crit-Line® monitor (CLM) (e.g., as described herein).

In some examples, the vascular access device has been implanted in anticipation of administering a hemodialysis treatment.

In some examples, the vascular access device has been implanted in less than 180, 120, or 60 minutes prior to administering a hemodialysis treatment.

In some examples, the subject has undergone at least one hemodialysis treatment.

In some examples, the subject has a renal disease. The subject may have an acute renal disease. The subject may have a chronic renal disease.

In some examples, the subject has kidney failure.

In some examples, the subject has abnormal (e.g., impaired) kidney function.

According to at least one aspect, a method of improving the maintenance of a medical record for a subject is provided. The method includes directly or indirectly acquiring an acquired value for a parameter that is a function of oxygen saturation ($SO_2$) of a sample of blood in or obtained from the VAD, performing an evaluation of the acquired value, at least by comparing the acquired value with one or more reference values, responsive to the evaluation of the acquired value, assigning an identity classification to the VAD, wherein the identity classification is one of a central venous catheter (CVC), an arteriovenous access device (AVA), or another class of VAD, and entering the classification into the medical record.

In some examples, one or more steps of the method are automated.

In some examples, one or more steps of the method are computer implemented.

According to at least one aspect, a method of maintaining a medical record for a subject is provided. The method includes directly or indirectly acquiring an acquired value for a parameter that is a function of oxygen saturation ($SO_2$) of a sample of blood in or obtained from the VAD, performing an evaluation of the acquired value, at least by comparing the acquired value with one or more reference values, responsive to the evaluation of the acquired value, assigning an identity classification to the VAD, wherein the identity classification is one of a central venous catheter (CVC), an arteriovenous access device (AVA), or another class of VAD, and entering the classification into the medical record.

In some examples, one or more steps of the method are automated.

In some examples, one or more steps of the method are computer implemented.

According to at least one aspect, a system is provided that includes a vascular access device (VAD), a probe configured for the measurement of a value for a parameter that is a function of oxygen saturation ($SO_2$) in blood in or that has passed through the VAD, and configured to generate a signal for the value, and a computer configured so as to receive the signal, evaluate the signal, and provide an output responsive to the evaluation.

According to at least one aspect, a blood monitoring system is provided. The blood monitoring system includes a sensor configured to measure a value indicative of an oxygen saturation ($SO_2$) in blood obtained from a vascular access device (VAD) in a dialysis patient. The blood monitoring system further includes a processor coupled to the probe, the processor being configured to receive the value from the probe and identify a type of vascular access in the dialysis patient based on the value.

In some examples, the blood monitoring system further includes a display coupled to the processor. The processor may be further configured to display the type of vascular access via the display.

In some examples, the type of vascular access includes at least one of a central venous catheter and an arteriovenous access device.

In some examples, the processor is communicatively coupled to a dialysis machine. In these examples, the processor may be further configured to provide information indicative of the type of vascular access in the dialysis patient to the dialysis machine.

In some examples, the blood monitoring system is configured to provide dialysis treatment to the patient.

In some examples, is communicatively coupled to a central server storing an electronic health record (EHR) of the dialysis patient. In these examples, the processor may be further configured to provide information indicative of the type of vascular access in the dialysis patient to the central server to update the EHR of the dialysis patient.

DETAILED DESCRIPTION OF THE INVENTION

Hemoglobin is the protein in red blood cells that carries oxygen from the lungs to the body's tissues and returns carbon dioxide from the tissues back to the lungs. Oxygen saturation ($SO_2$) is the fraction of oxygen-saturated hemoglobin relative to total hemoglobin (unsaturated+saturated) in the blood (commonly expressed as a percentage of hemoglobin molecules that transport oxygen in proportion to the total number of hemoglobin molecules). The normal oxygen saturation of venous blood is about 60-80%, reflecting the average amount of oxygen remaining after all tissues in the body have removed oxygen from hemoglobin. Conversely, the normal oxygen saturation of arterial blood is >90%, reflecting the oxygen saturation of the blood after it is re-oxygenated in the pulmonary capillary and before the tissues have removed oxygen from hemoglobin. With a CVC access, venous blood is pumped through the extracorporeal circuit of the dialysis device. With an AVA, arterial blood is pumped through the extracorporeal circuit.

Figure 1:
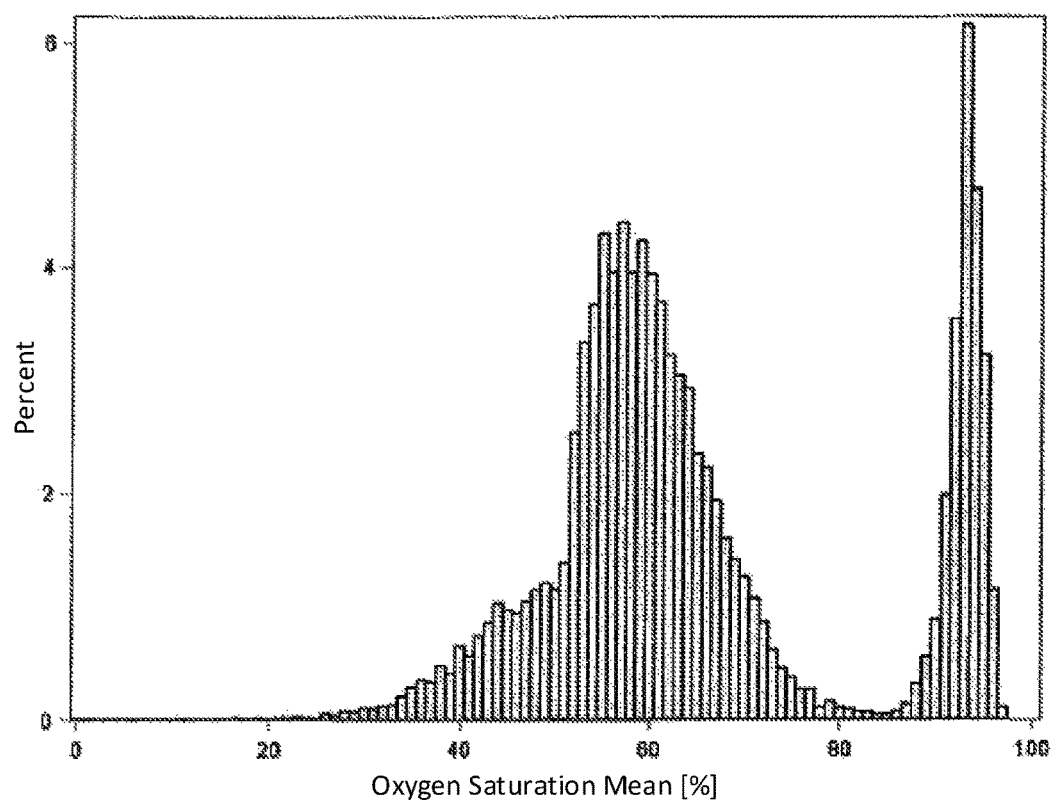
FIG. 1 is an example of a histogram depicting a mean oxygen saturation ($SO_2$) of extracorporeal blood derived from dialysis patients' vascular access, where the dialysis patients each had a documented central venous catheter vascular access.
Figure 2:
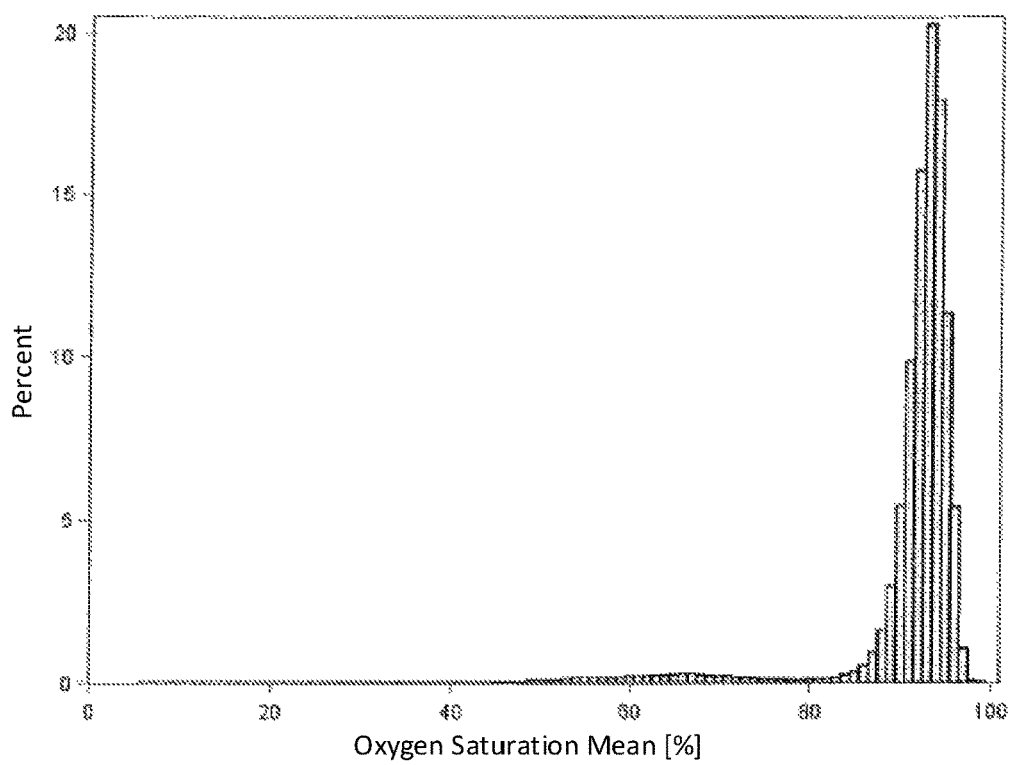
FIG. 2 is an example of a histogram depicting a mean oxygen saturation ($SO_2$) of extracorporeal blood derived from dialysis patients' vascular access, where the dialysis patients each had a documented arteriovenous access.

Different types of vascular access devices (e.g., a central venous catheter (CVC) versus an arteriovenous access (AVA)) are associated with different clinical outcomes for patients on dialysis, such as varying rates of morbidity and mortality. Therefore, the type of vascular access device can be used, inter alia, in predictive modeling of dialysis patient outcomes. However, for such use, accurate documentation of vascular access (e.g., a central venous catheter (CVC) versus an arteriovenous access (AVA)) is critical. Typically, the identity of a patient's vascular access is entered into a patient's electronic health record (EHR) manually, by medical staff, but as demonstrated herein, this manual process is subject to errors. For example, techniques disclosed herein identified that some patients with a CVC as their documented vascular access had high $SO_2$ levels, which are not indicative of venous blood derived from a CVC access. This discrepancy was a clear indication that the identity of the subject's vascular access in the EHR was incorrect (FIG. 1). Likewise, techniques disclosed herein identified that some patients with an AVA as the documented vascular access had low $SO_2$ levels, which are not indicative of arterial blood (FIG. 2) generally derived from an AVA. Again, this discrepancy was a clear indication that the identity of the patient's vascular access in the EHR was incorrect. It is clear from the data presented herein that the manual approach to vascular access identification and recordation is not completely accurate.

Thus, some aspects of the present disclosure are based in part on the use of the differential $SO_2$ of blood obtained from a CVC and an AVA, to identify the type of vascular access device that a subject has. Accordingly, the present disclosure involves, inter alia, methods of identifying a vascular access device that include measuring the oxygen saturation in a dialysis patient's extracorporeal blood, determining an access type, comparing that access type to the one recorded in a patient's electronic health record, and if an error is discovered, either flagging that error for human review or automatically correcting it.

Definitions

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third-party laboratory that directly acquired the physical entity or value). Directly acquiring a physical entity includes performing a process that includes a physical change in a physical substance, e.g., a starting material. Exemplary changes include—but are not limited to—making a physical entity from two or more starting materials, shearing or fragmenting a substance, separating or purifying a substance, combining two or more separate entities into a mixture, and/or performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

The terms "patient," "subject," "individual," and "host," as used synonymously herein, refer to either a human or a non-human animal having a vascular access or having had a vascular access.

The terms "oxygen saturation" and "$SO_2$," as used synonymously herein, refer to the fraction of oxygen-saturated hemoglobin relative to total hemoglobin (unsaturated+saturated) in the blood. $SO_2$ is commonly expressed as a percentage of hemoglobin molecules that transport oxygen in proportion to the total number of hemoglobin molecules. For example, a hemoglobin molecule can carry a maximum of four oxygen molecules. 1000 hemoglobin molecules can carry a maximum of 4000 oxygen molecules; if they were collectively carrying 3600 oxygen molecules, then the oxygen saturation level would be (3600/4000)*100% or 90%.

The terms "venous oxygen saturation" and "$SvO_2$," as used synonymously herein, refer to the oxygen saturation of venous blood (i.e., the average amount of oxygen remaining after all tissues in the body have removed oxygen from the hemoglobin). $SvO_2$ reflects the oxygen saturation of the blood before it is re-oxygenated in the pulmonary capillary. $SvO_2$ is commonly expressed as a percentage of hemoglobin molecules that transport oxygen in proportion to the total number of hemoglobin molecules. Under general medical standards, a normal human $SvO_2$ is generally within the range of about 60-80%.

The terms "arterial oxygen saturation" and "$SaO_2$," as used synonymously herein, refer to the oxygen saturation of arterial blood (i.e., the average amount of oxygen before all tissues in the body have removed oxygen from the hemoglobin). $SaO_2$ reflects the oxygen saturation of the blood after it is re-oxygenated in the pulmonary capillary and before the tissues have removed oxygen from hemoglobin. $SaO_2$ is commonly expressed as a percentage of hemoglobin molecules that transport oxygen in proportion to the total number of hemoglobin molecules. Under general medical standards, a normal human $SaO_2$ is generally greater than about 90%.

The terms "hemodialysis" and "dialysis," as used synonymously herein, refer to the process in which blood is drawn from a subject into a dialysis machine, circulated through the machine, and then returned to the patient. Hemodialysis generally requires a vascular access device to provide one or more reliable sites where the bloodstream can be easily accessed each time dialysis is administered (e.g., generally one or more times per week).

The terms "vascular access" and "vascular access device," as used synonymously herein, refer to a catheter, cannula, or other instrument used to obtain access to a subject's vascular system, i.e., venous or arterial access. The instrument is generally fixed in the subject's body. Vascular access devices are typically implanted when access to the vascular system is needed over a significant period of time (e.g., weeks, months, or permanently). Exemplary vascular access devices include, but are not limited to, central venous catheter (CVC) and arteriovenous access (AVA) (e.g., arteriovenous graft and arteriovenous fistula). See also, e.g., Santoro D. *Vascular access for hemodialysis: current perspectives*. Int J Nephrol Renovasc Dis. 2014 Jul. 8; 7:281-94; Gibbons, C. P. *Primary Vascular Access* European Journal of Vascular and Endovascular Surgery, Volume 31, Issue 5, 523-529; Prabir Roy-Chaudhury, Vikas P. Sukhatme, and Alfred K. Cheung, *Hemodialysis Vascular Access Dysfunction: A Cellular and Molecular Viewpoint*, JASN Apr. 2006 17: 1112-1127; Mickley V1. Central vein obstruction in vascular access, *Eur J Vasc Endovasc Surg*. 2006 October; 32 (4):439-44. Epub 2006 Jun. 9, the entire contents of each of which is incorporated by reference herein.

The terms "central venous catheter" and "CVC," as used synonymously herein, refer to an artificial tube (usually plastic) which is inserted into a large vein, usually in the neck. Where a CVC is used for dialysis, an external portion of the catheter is exposed on the chest wall that allows the tubing for the dialysis machine to be connected. See e.g., Santora, supra.

The terms "arteriovenous access" and "AVA," as used synonymously herein, include an arteriovenous fistula or an arteriovenous graft. An arteriovenous fistula is a connection made between an artery and a vein. The artificial connection allows the vein to become larger and for the walls of the vein to thicken, a process termed "maturation." A mature fistula makes it easier for the vein to be punctured repeatedly for dialysis. An arteriovenous graft is a piece of artificial tubing, generally made out of polytetrafluoroethylene (e.g., Teflon®) or fabric, that is attached on one end to an artery, and on the other end to a vein. The tube is placed entirely under the skin and the tube itself is punctured during dialysis. See e.g., Santora, supra.

Devices and Methods of Determining $SO_2$

Methods described herein include directly or indirectly acquiring one or more value(s) of oxygen saturation ($SO_2$) of extracorporeal blood obtained from a subject's vascular access device. Methods of determining $SO_2$ are standard and known to those of skill in the art. For example, a blood gas analyzer can be used to measure saturated oxygen in extracorporeal blood derived from the subject's vascular access. Blood gas analyzers are standard equipment in a clinical laboratory testing facilities and dialysis treatment centers. Exemplary commercially available blood gas analyzers include, for example: Seimens' RAPIDLab 1200, 500, and 248/348 Systems; Medica's EasyBloodGas System; Optimedical's OPTIC®, CCA-TS2 Blood Gas and Electrolyte Analyzer. $SO_2$ can also be measured using Crit-line® (commercially available from Fresenius Medical Care). For exemplary methods also see, e.g., the following references, the entire contents of each of which are incorporated by reference herein: Jones J G, Bembridge J L, Sapsford D J, Turney J H. *Continuous measurements of oxygen saturation during haemodialysis*. Nephrol Dial Transplant. 1992; 7 (2):110-116; Harrison L E, Selby N M, McIntyre C W. *Central Venous Oxygen Saturation: A Potential New Marker for Circulatory Stress in Haemodialysis Patients?* Nephron Clin Pract. 2014; 128 (1-2):57-60; and Hasan A. *Handbook of Blood Gas/Acid-Base Interpretation*. Springer, 2009.

Assessment of $SO_2$ Values

As described herein, a subject's vascular access device is identified as a CVC if the $SO_2$ of the sample of extracorporeal blood obtained from the subject's vascular access device, assessed using the methods disclosed herein, meets (e.g., corresponds with, satisfies, or falls within) a predetermined range (e.g., a range including the minimum and maximum values of the range, and in some cases plus or minus a window of variability (e.g., +/−0.5%, +/−1%, +/−5%, or +/−10%) or value (e.g., an average value (or other value of central tendency) plus or minus a window of variability (e.g., +/−0.5%, +/−1%, +/−5%, or +/−10%)). For example, a subject's vascular access device may be identified as a CVC if the $SO_2$ of a sample of extracorporeal blood obtained from the subject's vascular access device falls within the $SO_2$ range normally indicative of venous blood. In some instances, the $SO_2$ is indicative of venous blood if the $SO_2$ of the sample is within 60-80%, 61-80%, 62-80%, 63-80%, 64-80%, 65-80%, 66-80%, 67-80%, 68-80%, 69-80%, 70-80%, 65-75%, 65-76%, 65-77%, 65-78%, or 65-79% (and in some cases plus or minus a window of variability (e.g., +/−0.5%, +/−1%, +/−5%, or +/−10%)) of total hemoglobin saturated with oxygen.

In some embodiments, the activity of the $SO_2$ of the sample of extracorporeal blood obtained from the subject's vascular access device is expressed as a single value (e.g., an average value (or other value of central tendency) plus or minus a window of variability (e.g., +/−0.5%, +/−1%, +/−5%, or +/−10%)) and the $SO_2$ normally indicative of venous blood is expressed as a range (e.g., a range including the minimum and maximum values of the range, and in some cases plus or minus a window of variability (e.g., +/−0.5%, +/−1%, +/−5%, or +/−10%)). For example, a subject's vascular access device may be identified as a CVC if the $SO_2$ of a sample of extracorporeal blood obtained from the subject's vascular access device, assessed using the methods disclosed herein and expressed as an average value plus or minus a window of variability (e.g., +/−0.5%, +/−1%, +/−5%, or +/−10%) falls within a predetermined range (e.g., a range including the minimum and maximum values of the range, and in some cases plus or minus a window of variability (e.g., +/−0.5%, +/−1%, +/−5%, or +/−10%)).

In some embodiments, the activity of the $SO_2$ of the sample of extracorporeal blood obtained from the subject's vascular access device is expressed as a range (e.g., a range including the minimum and maximum values of the range, and in some cases plus or minus a window of variability (e.g., +/−0.5%, +/−1%, +/−5%, or +/−10%)), and the $SO_2$ normally indicative of venous blood is expressed as a range (e.g., a range including the minimum and maximum values of the range, and in some cases plus or minus a window of variability (e.g., +/−0.5%, +/−1%, +/−5%, or +/−10%)). For example, a subject's vascular access device may be identified as a CVC if the $SO_2$ of the sample of extracorporeal blood obtained from the subject's vascular access device, assessed using the methods disclosed herein and expressed as a range (e.g., a range including the minimum and maximum values of the range, and in some cases plus or minus a window of variability (e.g., +/−0.5%, +/−1%, +/−5%, or +/−10%)) falls within a predetermined range (e.g., a range including the minimum and maximum values of the range, and in some cases plus or minus a window of variability (e.g., +/−0.5%, +/−1%, +/−5%, or +/−10%)). A subject's vascular access device may be identified as an AVA if the $SO_2$ of the sample of extracorporeal blood obtained from the subject's vascular access device, assessed using the methods disclosed herein, meets (e.g., corresponds with, satisfies, or falls within) a predetermined range (e.g., a range including the minimum and maximum values of the range, and in some cases plus or minus a window of variability (e.g., +/−0.5%, +/−1%, +/−5%, or +/−10%) or value (e.g., an average value (or other value of central tendency) plus or minus a window of variability (e.g., +/−0.5%, +/−1%, +/−5%, or +/−10%)). For example, a subject's vascular access device may be identified as an AVA if the $SO_2$ of the sample of extracorporeal blood obtained from the subject's vascular access device falls within the $SO_2$ normally indicative of arterial blood. In some instances, the $SO_2$ is indicative of venous blood if the $SO_2$ of the sample is within 90-100%, 91-100%, 92-100%, 93-100%, 94-100%, 95-100%, 96-100%, 97-100%, 98-100%, or 99-100% (and in some cases plus or minus a window of variability (e.g., +/−0.5%, +/−1%, +/−5%, or +/−10%)) of total hemoglobin saturated with oxygen.

In some embodiments, the activity of the $SO_2$ of the sample of extracorporeal blood obtained from the subject's vascular access device is expressed as a single value (e.g., an average value (or other value of central tendency) plus or minus a window of variability (e.g., +/−0.5%, +/−1%, +/−5%, or +/−10%)) and the $SO_2$ normally indicative of arterial blood is expressed as a range (e.g., a range including the minimum and maximum values of the range, and in some cases plus or minus a window of variability (e.g., +/−0.5%, +/−1%, +/−5%, or +/−10%)). For example, a subject's vascular access device may be identified as an AVA if the $SO_2$ of the sample of extracorporeal blood obtained from the subject's vascular access device, assessed using the methods disclosed herein and expressed as an average value plus or minus a window of variability (e.g., +/−0.5%, +/−1%, +/−5%, or +/−10%) falls within a predetermined range (e.g., a range including the minimum and maximum values of the range, and in some cases plus or minus a window of variability (e.g., +/−0.5%, +/−1%, +/−5%, or +/−10%)).

In some embodiments, the activity of the $SO_2$ of the sample of extracorporeal blood obtained from the subject's vascular access device is expressed as a range (e.g., a range including the minimum and maximum values of the range, and in some cases plus or minus a window of variability (e.g., +/−0.5%, +/−1%, +/−5%, or +/−10%)), and the $SO_2$ normally indicative of arterial blood is expressed as a range (e.g., a range including the minimum and maximum values of the range, and in some cases plus or minus a window of variability (e.g., +/−0.5%, +/−1%, +/−5%, or +/−10%)). For example, a subject's vascular access device may be identified as an AVA if the $SO_2$ of the sample of extracorporeal blood obtained from the subject's vascular access device, assessed using the methods disclosed herein and expressed as a range (e.g., a range including the minimum and maximum values of the range, and in some cases plus or minus a window of variability (e.g., +/−0.5%, +/−1%, +/−5%, or +/−10%)) falls within a predetermined range (e.g., a range including the minimum and maximum values of the range, and in some cases plus or minus a window of variability (e.g., +/−0.5%, +/−1%, +/−5%, or +/−10%)).

An acquired value or values of the $SO_2$ of the sample of extracorporeal blood obtained from the subject's vascular access device, or a determination of the identity of the subject's vascular access, or a predetermined value or range as described herein, can be recorded, e.g., using a recordable medium (e.g., on paper, in a non-transitory computer readable medium, in an electronic health record (EHR), and/or in a paper health record).

Renal Disorders

Methods and systems described herein may be used in subjects diagnosed with a kidney (i.e., renal) disorder (e.g., a kidney disorder requiring dialysis). A used herein, the terms "kidney disorder" and "renal disorder" are used synonymously. This includes diseases where the kidneys are not able to sufficiently eliminate metabolic waste products (e.g., creatine and/or urea nitrogen). Exemplary renal disorders include, but are not limited to, kidney failure, kidney cancer, impaired kidney function, renal insufficiency, acute kidney disease, chronic kidney disease, end stage kidney disease, and kidney cysts.

Example Method of Identifying a Vascular Access Device

Figure 3:
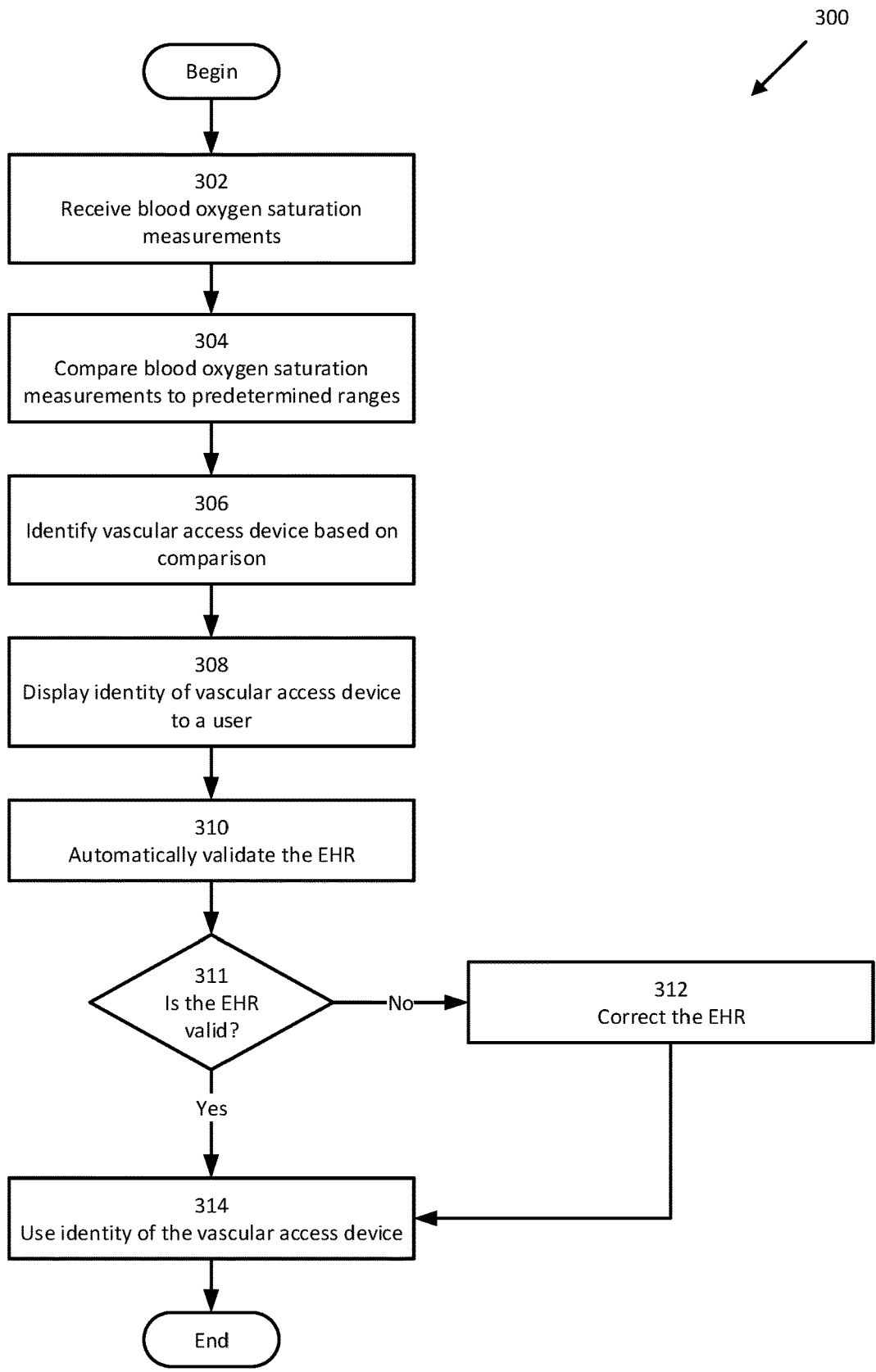
FIG. 3 is a flow diagram of an example method of identifying a type of vascular access device in a patient, according to an embodiment.

The following example shown in FIG. 3 illustrates an exemplary method 300 of identifying a type of vascular access device in a dialysis patient, which may include validating a previous identification of the vascular access device. The method may be performed by, for example, a blood monitoring device such as the Crit-line® monitor (commercially available from Fresenius Medical Care). Aspects of the Crit-line® monitor, according to an embodiment, are described in U.S. Pat. Nos. 5,372,136, 8,130,369, 9,370,324, and U.S. Pat. No. 9,173,988, all of which are incorporated herein by reference.

In act 302, the blood monitoring device receives measurements of the $SO_2$ of extracorporeal blood obtained from the subject's vascular access device. The blood monitoring device may receive these measurements during, for example, the first hour of a dialysis treatment. The measurements can be directly acquired through the use of a sensor configured to measure the $SO_2$ level of blood including, for example, a pulse oximeter, a standard blood gas analyzer, or another suitable device.

In act 304, the blood monitoring device may compare one or more measurements obtained in act 302 to a predetermined range of normal $SaO_2$ and $SvO_2$ levels (i.e., considered normal by standard medical practice), e.g., 90-100% and 60-80% (percentage of total hemoglobin saturated with oxygen), respectively. It is appreciated that the blood monitoring device may, in some examples, determine an average of multiple measurements of $SO_2$ levels and compare the average to the predetermined ranges. In other examples, a predetermined threshold $SO_2$ level may be used in conjunction with or in place of the predetermined ranges.

In act 306, the blood monitoring device identifies the type of vascular access in the patient based on the comparison performed in act 304. For example, the medical device may determine that the vascular access device in the patient is an AVA responsive to the $SO_2$ of the patient being within the predetermined range of $SaO_2$ (e.g., 97%). Conversely, the blood monitoring device may determine that the vascular access device in the patient is a CVC responsive to the $SO_2$ of the patient being within the predetermined range of $SvO_2$ (e.g., 75%).

In act 308, the blood monitoring device may display the identified vascular access device in the patient to a user (e.g., a physician or a nurse). Displaying the identified vascular access device may allow the user to, for example, compare the identity of the patient's vascular access with the patient's EHR to validate the EHR. Alternatively or additionally, in act 310, the blood monitoring device may communicate directly with, for example, a central server at the medical facility to automatically validate the EHR. An example of a system for identifying and validating vascular access devices is described below with respect to FIG. 5.

In act 311, the blood monitoring device or another component may determine whether the vascular access device listed in the patient's HER is valid, i.e., consistent with the identification obtained using the methods described herein. If the vascular access listed in the patient's EHR is inconsistent with the identification obtained using the methods described herein, then in act 312, the blood monitoring device (or a user of the blood monitoring device) can correct the inconsistency in the EHR to reflect the correct identity of the vascular access device or flag the inconsistency for a user or caregiver to review and correct. In act 314, the identity of the vascular access device (as validated and optionally corrected as described above) can subsequently be used in diagnosis, treatment, and/or in another medical process. For example, the identity of the vascular access device may be used in a method of assessing (e.g., predicting) the prognosis of a disorder (e.g., a renal disorder), wherein the subject has been diagnosed with said disorder (e.g., a renal disorder). Validation and (if necessary) correction of the identity of the vascular access device, as described above, helps ensure that the correct identity of the vascular access device is used, thus improving the quality of the diagnosis, treatment, and/or other medical process.

Therefore, the methods described herein provide for, inter alia, methods to identify a vascular access device, methods to validate the identity of a vascular access device, and methods to detect and correct an inaccurate the identity of a vascular access device.

Example Blood Monitoring Device

Figure 4:
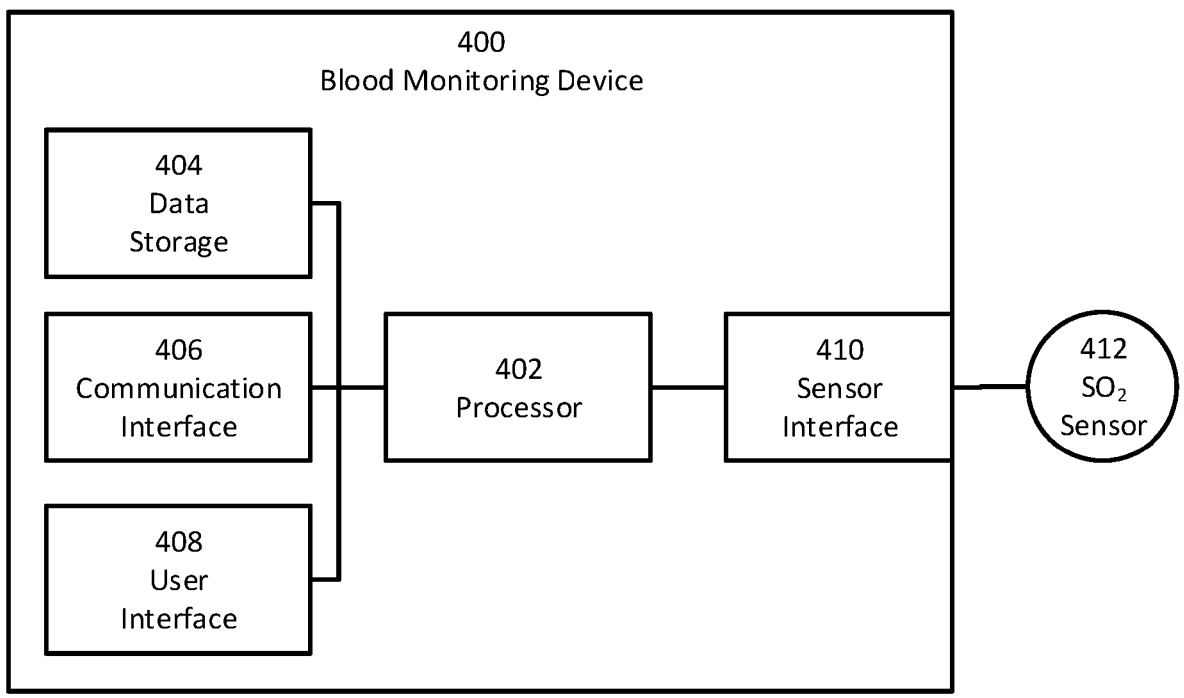
FIG. 4 is a block diagram of an example blood monitoring device, according to an embodiment.

As discussed above with regard to FIG. 3, a blood monitoring device is provided that identifies the type of vascular access in the patient based on the $SO_2$ level of the blood of the patient. FIG. 4 illustrates an example implementation of such a blood monitoring device 400. As shown in FIG. 4, the blood monitoring device 400 includes one or more processors 402, data storage 404, a communication interface 406, a user interface 408, and a sensor interface 410 that may be coupled to an $SO_2$ sensor 412. It is appreciated that the particular architecture shown in FIG. 4 is for illustration only and other architectures may be employed.

According to the example illustrated in FIG. 4, a processor 402 is coupled to the data storage 404, the communication interface 406, the user interface 408, and the sensor interface 410. The processor 402 executes a series of instructions that result in manipulated data which are stored in and retrieved from the data storage 404. According to a variety of examples, the processor 402 is a commercially available processor such as a processor manufactured by Intel, Advanced Micro Devices (AMD), Motorola, and Freescale. However, the processor 402 may be any type of processor, multiprocessor or controller, whether commercially available or specially manufactured.

In addition, in some examples, the processor 402 may be configured to execute an operating system. The operating system may provide platform services to application software, such as any application software configured to perform the method 300 to identify a type of vascular access in the patient as described above. These platform services may include inter-process and network communication, file system management and standard database manipulation. One or more of many operating systems may be used, and examples are not limited to any particular operating system or operating system characteristic. In some examples, the processor 402 may be configured to execute a real-time operating system (RTOS), such as RTLinux, or a non-real time operating system, such as BSD or GNU/Linux.

The data storage 404 includes a non-transitory computer-readable and writeable nonvolatile data storage medium configured to store non-transitory instructions and data. In addition, the data storage 404 includes processor memory that stores data during operation of the processor 404. In some examples, the processor memory includes a relatively high performance, volatile, random access memory such as dynamic random-access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the data storage 404 may include executable programs or other code that can be executed by the processor 402. The instructions may be persistently stored as encoded signals, and the instructions may cause the processor 402 to perform the functions described herein. The data storage 404 may include information that is recorded, on or in, the medium, and this information may be processed by the processor 402 during execution of instructions. The data storage 404 may also include, for example, data specifying the particular predetermined threshold(s) and/or range(s) of $SO_2$ associated with each type of vascular access device. The medium may, for example, be optical disk, magnetic disk or flash memory, among others, and may be permanently affixed to, or removable from, the blood monitoring device 400.

As shown in FIG. 4, the blood monitoring device 400 includes several system interface components 406 and 410. Each of these system interface components is configured to exchange data with one or more specialized devices that may be located within a housing of the blood monitoring device or elsewhere. The components used by the interfaces 406 and 410 may include hardware components, software components or a combination of both. Within each interface, these components physically and logically couple the blood monitoring device 400 to the specialized devices. These specialized devices may include, for example, various sensors and computer networking devices.

According to various examples, the hardware and software components of the interfaces 406 and 410 implement a variety of coupling and communication techniques. In some examples, the interfaces 406 and 410 use leads, cables or other wired connectors as conduits to exchange data between the blood monitoring device 400 and specialized devices. In other examples, the interfaces 406 and 410 communicate with specialized devices using wireless technologies such as radio frequency or infrared technology.

As discussed above, the system interface components 406 and 410 shown in the example of FIG. 4 support different types of specialized devices. The components of the sensor interface 410 couple the processor 402 to one or more sensors to, for example, gather information regarding the $SO_2$ level. For example, the sensor interface 410 may couple the processor 402 to an $SO_2$ sensor as illustrated by $SO_2$ sensor 412. It is appreciated that other sensors may be coupled to the sensor interface 410 in place of or in conjunction with the $SO_2$ sensor 412.

In addition, the components of the communication interface 406 couple the processor 402 to external systems via either a wired or wireless communication link. For example, the communication interface 406 may enable the blood monitoring device 400 to communicate with a hemodialysis machine to provide information regarding the type of vascular access in the patient. In other examples, the communication interface 406 may enable the blood monitoring device 400 to communicate with one or more central servers of a medical center (e.g., a hospital) to update the EHR of the patient. For example, the blood monitoring device 400 may communicate with one or more edge devices and/or another type of server as part of a system as described below with respect to FIG. 5.

According to a variety of examples, the communication interface 406 supports a variety of standards and protocols, examples of which include Universal Serial Bus (USB), Transmission Control Protocol/Internet Protocol (TCP/IP), Ethernet, Bluetooth, Zigbee, Controller Area Network (CAN) bus, Internet Protocol (IP), IP version 6 (IPV6), User Datagram Protocol (UDP), Delay/Disruption Tolerant Networking (DTN), Hypertext Transfer Protocol (HTTP), HTTP Secure (HTTPS), File Transfer Protocol (FTP), Simple Network Management Protocol (SNMP), Code Division Multiple Access (CDMA), National Marine Electronics Association (NMEA), and Global System for Mobile Communications (GSM). It is appreciated that the communication interface 406 of the blood monitoring device 400 may enable communication between other devices within a certain range.

The user interface 408 shown in FIG. 4 includes a combination of hardware and software components that allow the blood monitoring device 400 to communicate with an external entity, such as a physician, a nurse, or another user. The components of the user interface 408 can provide information to external entities and/or receive instructions from external entities. Examples of the components that may be employed within the user interface 408 include keypads, buttons, microphones, touch screens, display screens, and speakers. In some examples, the user interface 408 may include a display and present, via the display, information regarding the identified type of vascular access to the user.

It is appreciated that the blood monitoring device 400 is not limited to monitoring-only devices. In some examples, the blood monitoring device 400 may be a treatment device configured to provide at least one form of treatment to the patient. For example, the blood monitoring device 400 may be a dialysis machine constructed to provide dialysis treatment to the patient. In this example, the dialysis machine may identify the type of vascular access in the patient using one or more of the methods described herein and adjust the treatment provided to the patient based on the type of vascular access in the patient.

Figure 5:
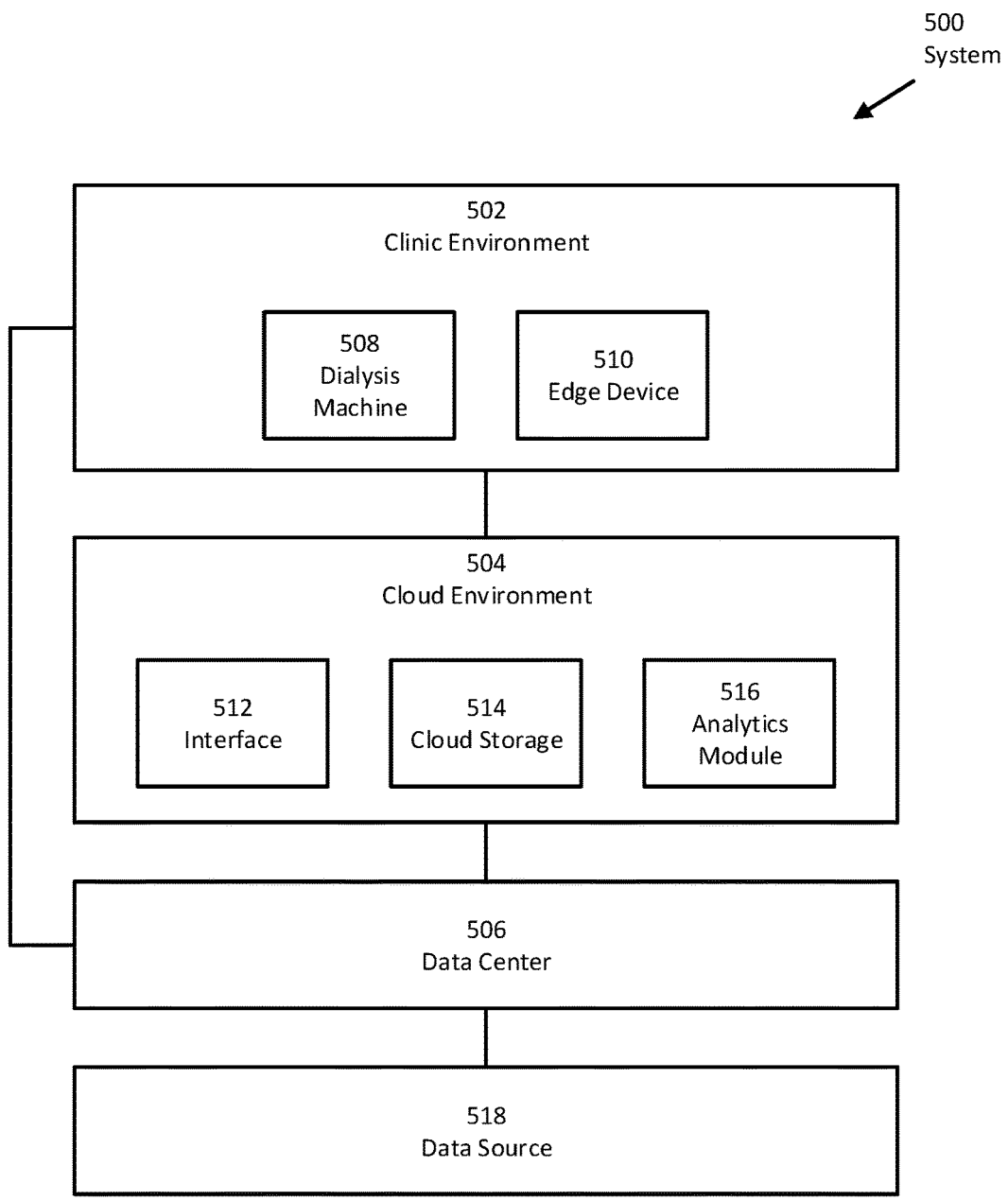
FIG. 5 is a block diagram of an example system according to an embodiment.

FIG. 5 is a block diagram of an example system 500 according to an embodiment. In an embodiment, system 500 may include more or fewer components than the components illustrated in FIG. 5. The components illustrated in FIG. 5 may be local to or remote from each other. The components illustrated in FIG. 5 may be implemented in software and/or hardware. Each component may be distributed over multiple applications and/or machines. Multiple components may be combined into one application and/or machine. Operations described with respect to one component may instead be performed by another component.

As illustrated in FIG. 5, system 500 includes one or more components in a clinic environment 502 (e.g., a hospital, dialysis center, or other type of clinic). In some embodiments, a clinic environment 502 may include the home of a patient who undergoes in-home dialysis treatment. Components of clinic environment 502 may be distributed across multiple physical locations and configured to communicate with each other using one or more secure networking protocols, for example via a virtual private network (VPN), tunnel, HTTPS, and/or another type of secure networking protocol.

Clinic environment 502 includes one or more dialysis machines 508. Dialysis machine 508 is configured to perform dialysis and obtain crit-line data such as hematocrit (HCT), relative blood volume (RBV), oxygen ($O_2$), and/or other data. In addition, dialysis machine 508 may be configured to collect information about dialysis machine 508's operations, such as settings, alarms, activity logs, etc. Dialysis machine 508 may include a computer system configured to perform one or more of these functions. For example, dialysis machine 508 may include a computer system that implements Clinical Data eXchange™ (CDX) technology. Dialysis machine 508 may be a model produced by Fresenius Medical Care, for example a 2008T dialysis machine or another model, or another vendor. Clinic environment 502 may include dialysis machines 508 from multiple vendors.

In an embodiment, dialysis machine 508 is configured to transmit data (e.g., crit-line data, operational data, and/or other data) to an edge device 510. Dialysis machine 508 may be configured to transmit data to edge device 510 periodically, for example every ten seconds or at other intervals and/or based on particular transmission criteria (e.g., responsive to detecting that new data is available for transmission). Dialysis machine 508 may be configured to communicate with edge device 510 using one or more secure networking protocols, for example via a virtual private network (VPN), tunnel, HTTPS, and/or another type of secure networking protocol.

In an embodiment, edge device 510 includes hardware and/or software configured to perform calculations based on data received from dialysis machine 508 and/or transmit data (e.g., as received and/or as modified by one or more calculations) to one or more components outside of clinical environment 502. Edge device 510 may perform calculations as data are received, responsive to receiving the data, i.e., in "real time." Alternatively, edge device 510 may store data and subsequently perform calculations at particular intervals and/or when a threshold amount of data has been received. Edge device 510 may be configured to encrypt and/or otherwise secure data prior to transmission.

In an embodiment, edge device 510 is configured to transmit data to one or more components outside of clinical environment 502. For example, edge device 510 may be configured to transmit data to a cloud environment 504 via an interface 512. Cloud environment 504 may be an Internet-of-Things (IoT) cloud computing service. For example, cloud environment 504 may be an Amazon Web Services (AWS) Virtual Private Cloud (VPC), interface 512 may be an AWS IoT interface, and edge device 510 may be an AWS IoT Greengrass edge device hosting an AWS IoT Greengrass Core. One or more dialysis machines 508 may belong to an AWS IoT Greengrass group. Alternatively, another type of cloud computing service and/or configuration of components may be used. Edge device 510 may be configured to communicate with cloud environment 504 using one or more secure networking protocols, for example via a virtual private network (VPN), tunnel, HTTPS, and/or another type of secure networking protocol.

In an embodiment, cloud environment 504 stores data received from edge device 510 in cloud storage 514. Cloud storage 514 may be a data lake, i.e., a data repository configured to store data in a raw/native format until accessed at a later time. Data in a data lake may be assigned unique identifiers and tagged with metadata to facilitate subsequent searching and data retrieval. For example, cloud storage 514 may be an Amazon S3-based data lake. Alternatively, cloud storage 514 may be a data lake solution from another vendor and/or another type of data repository, such as a data warehouse.

In addition to data from clinical environment 502, cloud environment 504 may be configured to obtain and store data from a data center 506. Data center 506 includes one or more data repositories (not shown) storing data retrieved from one or more data sources 518. Specifically, data source(s) 518 may include one or more sources of patient clinical data, such as Fresenius Kidney Care (FKC) Chairside Information System, Fresenius Medical Care eCube Clinical (eCC) system, and/or one or more other sources of patient clinical data. Cloud environment 504 may use data from data center 506 to supplement and/or enhance analytics performed by analytics module 516, for example as described below. Cloud environment 504 may be configured to communicate with data center 506 using one or more secure networking protocols, for example via a virtual private network (VPN), tunnel, HTTPS, and/or another type of secure networking protocol.

In an embodiment, cloud environment 504 includes an analytics module 516 configured to analyze data from cloud storage 514 and optionally data center 506. Data analysis performed by analytics module 516 may include, for example: computations; analytics; machine learning algorithms; and/or another type of analysis or combination thereof. Cloud environment 504 may be configured to communicate the results of data analysis to clinic environment 502, for example via edge device 510. Specifically, cloud environment 504 may be configured to communicate instructions and/or alerts based on data analysis results to specific dialysis machines 508, to help direct and/or inform patient's diagnoses and/or treatments.

In one example, analytics module 516 receives crit-line data (e.g., oxygen saturation) for a patient from dialysis machine 508, via edge device 510, and EHR data for the same patient from data center 506. Analytics module 516 uses the crit-line data to identify the patient's vascular access device, using techniques described herein. If the identity of the vascular access device, as determined by analytics module 516, does not match the EHR data, then cloud environment 504 transmits an alert to dialysis machine 508 and/or instructions to change one or more operations of dialysis machine 508 based on the corrected identity of the vascular access device. In addition, cloud environment 504 may transmit updated information about the identity of the vascular access device to data center 506.

In an embodiment, one or more components of system 500 are implemented on one or more digital devices. The term "digital device" generally refers to any hardware device that includes a processor. A digital device may refer to a physical device executing an application or a virtual machine. Examples of digital devices include a computer, a tablet, a laptop, a desktop, a netbook, a server, a web server, a network policy server, a proxy server, a generic machine, a function-specific hardware device, a hardware router, a hardware switch, a hardware firewall, a hardware firewall, a hardware network address translator (NAT), a hardware load balancer, a mainframe, a television, a content receiver, a set-top box, a printer, a mobile handset, a smartphone, a personal digital assistant ("PDA"), a wireless receiver and/or transmitter, a base station, a communication management device, a router, a switch, a controller, an access point, and/or a client device.

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments described herein. Such equivalents are intended to be encompassed by the following claims.

What is claimed is:

1. A method for reducing errors in an electronic health record (EHR) of a subject comprising:
   directly or indirectly acquiring from a sensor configured to detect oxygen saturation ($SO_2$) an acquired value for a parameter that is a function of oxygen saturation of a sample of blood in or obtained from a vascular access device (VAD) disposed in the subject;
   performing an evaluation of the acquired value at least by comparing the acquired value with one or more reference values;
   based on the evaluation of the acquired value, assigning a first identity classification to the VAD, wherein the first identity classification is one of a central venous catheter (CVC), an arteriovenous access device (AVA), or another class of VAD;
   comparing a preexisting identity classification of the VAD to the first identity classification, the preexisting identity classification being part of a preexisting EHR of the subject; and responsive to determining that the preexisting identity classification does not match the first identity classification, automatically updating the preexisting identity classification to match the first identity classification.

2. The method of claim 1, further comprising assessing whether the acquired value is indicative of venous oxygen saturation ($SvO_2$) or arterial oxygen saturation ($SaO_2$).

3. The method of claim 1, further comprising addressing an inconsistency between the first identity classification and the preexisting identity classification, at least by flagging the inconsistency for human review.

4. The method of claim 1, wherein the one or more reference values comprises one or more of a predetermined value characteristic of arterial oxygen saturation ($SaO_2$) or a predetermined value characteristic of venous oxygen saturation ($SvO_2$).

5. The method of claim 1, further comprising memorializing the preexisting identity classification and the first identity classification of the VAD in a record associated with the patient.

6. One or more non-transitory computer-readable media storing instructions that, when executed by one or more processors, cause the one or more processors to perform operations comprising:
   directing a first device to directly or indirectly acquire from a sensor configured to detect oxygen saturation ($SO_2$) an acquired value for a parameter that is a function of oxygen saturation of a sample of blood in or obtained from a vascular access device (VAD) disposed in a subject;
   directing the first device to request, from a second device containing a preexisting electronic health record (EHR) of the subject, at least a part of the preexisting EHR that includes a preexisting identity classification of the VAD disposed in the subject;
   directing the first device to perform an evaluation of the acquired value at least by comparing the acquired value with one or more reference values;
   directing the first device to, based on the evaluation of the acquired value, assign a first identity classification to the VAD, wherein the first identity classification is one of a central venous catheter (CVC), an arteriovenous access device (AVA), or another class of VAD;
   directing the first device to compare the preexisting identity classification of the VAD to the first identity classification; and
   responsive to determining that the preexisting identity classification does not match the first identity classification, causing the first device to automatically transmit to the second device a request instructing the second device to update the preexisting identity classification to match the first identity classification.

7. The one or more non-transitory computer-readable media of claim 6, the operations further comprising assessing whether the acquired value is indicative of venous oxygen saturation ($SvO_2$) or arterial oxygen saturation ($SaO_2$).

8. The one or more non-transitory computer-readable media of claim 6, the operations further comprising addressing an inconsistency between the first identity classification and the preexisting identity classification, at least by performing one or more of (a) flagging the inconsistency for human review or (b) correcting the preexisting identity classification to reflect the first identity classification of the VAD.

9. The one or more non-transitory computer-readable media of claim 6, wherein the one or more reference values comprises one or more of a predetermined value characteristic of arterial oxygen saturation ($SaO_2$) or a predetermined value characteristic of venous oxygen saturation ($SvO_2$).

10. The one or more non-transitory computer-readable media of claim 6, the operations further comprising memorializing the preexisting identity classification and the first identity classification of the VAD in a record associated with the patient.

11. A blood monitoring system comprising:
    a first device configured to communicate with a second device, the second device including a preexisting electronic health record (EHR) of a dialysis patient, and the first device including a sensor configured to measure a value indicative of an oxygen saturation ($SO_2$) in blood obtained from a vascular access device (VAD) disposed in the dialysis patient;
    one or more processors; and
    one or more non-transitory computer-readable media storing instructions that, when executed by the one or more processors, cause the one or more processors to perform operations comprising:
      receiving, at the first device, the value from the sensor;
      determining a first identity classification of the VAD by identifying a type of the VAD based at least on the value;
      receiving, at the first device, at least a portion of the preexisting EHR;
      comparing a preexisting identity classification of the VAD, contained in the at least a portion of the preexisting EHR, to the first identity classification;
      responsive to determining that the preexisting identity classification does not match the first identity classification, causing the first device to automatically send a request to the second device requesting that the second device update the preexisting identity classification to match the first identity classification; and
      updating, at the second device, the preexisting identity classification to match the first identity classification.

12. The blood monitoring system of claim 11, further comprising a display, the operations further comprising displaying the type of the VAD via the display.

13. The blood monitoring system of claim 11, wherein the type of the VAD includes one or more of a central venous catheter (CVC) or an arteriovenous access device (AVA).

14. The blood monitoring system of claim 11, wherein the one or more processors are communicatively coupled to a dialysis machine.

15. The blood monitoring system of claim 14, the operations further comprising providing information indicative of the type of the VAD to the dialysis machine.

16. The blood monitoring system of claim 11, wherein the one or more processors are communicatively coupled to a central server storing the preexisting EHR of the dialysis patient.

17. The blood monitoring system of claim 16, the operations further comprising providing information indicative of the type of the VAD to the central server to update the preexisting EHR of the dialysis patient.

* * * * *